United States Patent
Leahy

(10) Patent No.: US 8,192,358 B2
(45) Date of Patent: Jun. 5, 2012

(54) DEVICE AND METHOD FOR USE IN SURGERY

(76) Inventor: Patrick Leahy, Dublin (IE)

(*) Notice: Subject to any disclaimer, the term of this patent is extended or adjusted under 35 U.S.C. 154(b) by 1256 days.

(21) Appl. No.: 10/553,941

(22) PCT Filed: Apr. 22, 2004

(86) PCT No.: PCT/EP2004/004381
§ 371 (c)(1),
(2), (4) Date: Mar. 20, 2007

(87) PCT Pub. No.: WO2004/093699
PCT Pub. Date: Nov. 4, 2004

(65) Prior Publication Data
US 2008/0091080 A1    Apr. 17, 2008

(30) Foreign Application Priority Data
Apr. 22, 2003    (IE) .................... S2003/0304

(51) Int. Cl.
*A61B 1/32* (2006.01)
(52) U.S. Cl. ........................................................ 600/207
(58) Field of Classification Search ........... 600/201–235
See application file for complete search history.

(56) References Cited

U.S. PATENT DOCUMENTS

| | | | |
|---|---|---|---|
| 3,831,587 A * | 8/1974 | Boyd ............................ 600/207 |
| 5,480,410 A * | 1/1996 | Cuschieri et al. ............. 606/213 |
| 5,522,791 A * | 6/1996 | Leyva ............................ 600/207 |
| 5,640,977 A * | 6/1997 | Leahy et al. ................... 128/897 |
| 5,899,208 A | 5/1999 | Bonadio |
| 6,077,288 A * | 6/2000 | Shimomura et al. .......... 606/185 |
| 6,142,936 A * | 11/2000 | Beane et al. ................... 600/207 |
| 6,440,063 B1 * | 8/2002 | Beane et al. ................... 600/207 |
| 7,294,103 B2 * | 11/2007 | Bertolero et al. ............. 600/207 |

OTHER PUBLICATIONS

International Search Report for PCT/EP2004/04381.

* cited by examiner

*Primary Examiner* — Eduardo C Robert
*Assistant Examiner* — Steven Cotroneo
(74) *Attorney, Agent, or Firm* — Gardner, Linn, Burkhart & Flory, LLP

(57) ABSTRACT

The present invention is concerned with a device and method for use in surgery, in particular hand assisted laparascopic surgery, the device comprising a flexible sleeve about one end of which is located a plurality of inflatable balloons, such that the sleeve may be located about a surgeon's forearm, with the balloons thus circumscribing the surgeon's wrist, the balloons being inflated once the surgeon's hand and wrist have been inserted into a surgical cavity, in order to distend the surgical cavity, thereby creating a space within which the surgical procedure may be performed.

20 Claims, 3 Drawing Sheets

DEVICE AND METHOD FOR USE IN SURGERY

The present invention relates to a device and a method for use in surgery, and in particular a device and a method for use in aiding hand assisted laparoscopic surgery and the like minimally invasive surgical procedures.

Although open surgery is still the most commonly performed type of surgery, it is gradually being replaced, where possible, by laparoscopic or hand assisted laparoscopic surgery, otherwise known as "keyhole" surgery. Open surgery requires the creation of a large incision or a plurality of incisions to gain access to surgical cavities such as the abdominal or thoracic cavities, the skin and tissue surrounding the incisions then being drawn back to expose the tissues/organs beneath. This type of open surgery therefore enables the surgeon to gain access, using both hands, to the site to be operated on, thereby facilitating a relatively straightforward surgical procedure. However, the benefits of open surgery are somewhat negated by the drawbacks associated with same. Primarily, the very nature of open surgery, requiring enlarged incisions and the displacement of significant amounts of tissue/organs in order to access the site in question, and perform the necessary surgery, results in significant post-operative trauma for the patient, and will also require an extended time for the incision(s) to heal. In addition, open surgery will also generally leave significant scarring, as a result of the enlarged incisions necessary.

For these reasons, when an operation may be performed using either open surgery or laparoscopic (keyhole) surgery, a patient will normally opt for the laparoscopic surgical procedure, due to the reduced trauma, recovery time, and scarring associated with same. However, laparoscopic surgery is a more specialised procedure, and one which is not capable of being performed by all surgeons, due to the highly specialised training and experience which are necessary.

The main problem associated with laparoscopic surgery is the lack of hands on contact by the surgeon, all of the surgical techniques, such as cutting, suturing, etc. being carried out remotely by means of laparoscopic surgical instruments and with the aid of fibre optic imaging systems. This problem can be significantly reduced by the use of hand assisted laparoscopic surgery, in which an incision is made, for example in the abdomen, which incision is dimensioned to permit a surgeon's hand access through the incision to the site on which surgery is to be performed, thereby allowing palpation and bio-physical feedback, thus greatly simplifying the laparoscopic surgical procedure.

However, this type of hand assisted laparoscopic surgery is not without its complications. During conventional laparoscopic surgery, a cavity within which surgery is being performed is generally distended by means of an insufflation gas, for example carbon dioxide, which is pumped into the surgical cavity in order to distend the area surrounding the surgical site, generally by means of a trocar and cannula arrangement. However, with hand assisted laparoscopic surgery, the access incision for the surgeon's hand provides a ready outlet for the insufflation gases, thereby preventing the necessary build-up of pressure within the gas in order to distend the surgical cavity.

One solution to this problem is set out in U.S. Pat. No. 5,640,977, on which the present applicant is a joint inventor. This document sets out a method and apparatus for hand assisted laparoscopic surgery, using a sleeve which must be sealed within the access wound, and which sleeve is provided with an inflatable cuff at the end of the sleeve distal the access wound, which cuff may be inflated such as to create a seal around the surgeon's forearm when located within the sleeve. In this way, the surgical cavity can be inflated, and although gas will initially leak through the access wound into the sleeve, the sleeve, being sealed against the surgeon's arm, will soon pressurise, thereby allowing the surgical cavity to be pressurised and therefore become distended.

However, the apparatus employed is complex and time consuming to use, and still requires the pumping of an insufflation gas such as carbon dioxide directly into the surgical cavity, which has been known to have adverse effects on the patient.

It is therefore an object of the present invention to mitigate the problems of the prior art by providing a surgical device for use in minimally invasive surgery such as hand assisted laparoscopic surgery.

The present invention therefore provides, in a first aspect, a surgical device for use in minimally invasive surgery, the device comprising a sleeve having an exit aperture and an entry aperture, the sleeve being shaped and dimensioned to permit the passage of a hand therethrough; and a distensible member secured to or formed integrally about the sleeve adjacent the exit aperture.

Preferably, the distensible member is generally annular in form and is located circumferentially about the sleeve adjacent the exit aperture, preferably at the exit aperture.

Alternatively, the distensible member comprises a plurality of distensible sections, for example balloons, arranged in an annular array, or in a series of annular arrays, adjacent the exit aperture, preferably at the exit aperture.

Preferably, the plurality of distensible sections may be individually, sequentially or simultaneously distended.

Preferably, the distensible member is secured to an exterior of the sleeve and is arranged to distend away from the arm, in use.

Preferably, the entry aperture has a larger cross sectional area than the exit aperture.

Preferably, the sleeve is substantially frustum shaped, more preferably substantially frusto-conically shaped.

Preferably, the sleeve is formed from a flexible material.

Preferably, the sleeve is shaped and dimensioned to permit the passage of a surgeon's hand therethrough and to accommodate at least a surgeon's forearm, in use.

Preferably, the sleeve is formed from a fluid impermeable material.

Preferably, the device comprises a reinforcing member located about the entry aperture of the sleeve, in order to hold open the entry aperture.

Preferably, the device further comprises means operable to seal the exit aperture from the entry aperture so that, in use, fluid passage from the exit aperture to the entry aperture is prevented.

Preferably, the sealing means comprises a one way valve.

Preferably, the sleeve is provided with a lubricant on an interior surface thereof.

Preferably, the device further comprises means for conveying a fibre optic camera along the length of the sleeve.

Preferably, the conveying means comprises a passage extending along the length of the sleeve.

Preferably, the device further comprises a cover releasably securable about the entry aperture, in order to fluid-tightedly seal the entry aperture.

Preferably, the sleeve is substantially transparent.

Preferably, the device further comprises a cuff located circumferentially or annularly about the sleeve adjacent the exit aperture of the sleeve.

According to a second aspect of the invention, there is provided a method of distending a surgical cavity, the method comprising the steps of;

providing a surgical device according to the first aspect of the invention;

passing a hand through the sleeve of the device;

inserting at least the distensible member of the device into the surgical cavity; and distending the distensible member.

As used herein, the term "sleeve" is intended to mean a substantially tubular element designed to accomodate another object of similar shape, and is preferably, but not essentially, formed from a flexible material in order to facilitate articulation of an object located within the sleeve. The sleeve may be mesh like in form, but is preferably formed from a closed or non-reticulated material.

As used herein, the term "hand" is intended to mean a human hand, as well as, a robotic or mechanical hand.

As used herein, the term "arm" is intended to mean a human arm or a portion thereof, for example the hand and forearm, or the entire arm from the hand to shoulder of a surgeon, but is also intended to cover a mechanical or robotic arm or the like.

As used herein, the term "distensible" is intended to mean the ability to distend or expand/deform/displace outwardly in order to be capable of enlarging a visceral space within a surgical cavity, in particular for the purposes of aiding laparoscopic surgical procedures, and may be achieved by inflation, mechanical displacement, or by any other suitable means.

As used herein, the term "inflation" is intended to mean the act of inflating an object with a fluid, whether with a gas or a liquid.

As used herein, the term "mitral valve" is intended to mean a non-return valve which is formed from a flexible tube having first and second ends. The first end is fluid tightly secured about the entire circumference thereof, to the sleeve. The second end of the flexible tube is freely suspended within the lumen of the sleeve, such that the valve is open when the pressure is the same between the first and the second ends or when the pressure is higher at the first end, compared to the second end, while the valve is closed when the pressure is higher at the second end, compared to the first end.

The present invention will now be described with reference to the accompanying drawings, in which.

Figure 1:
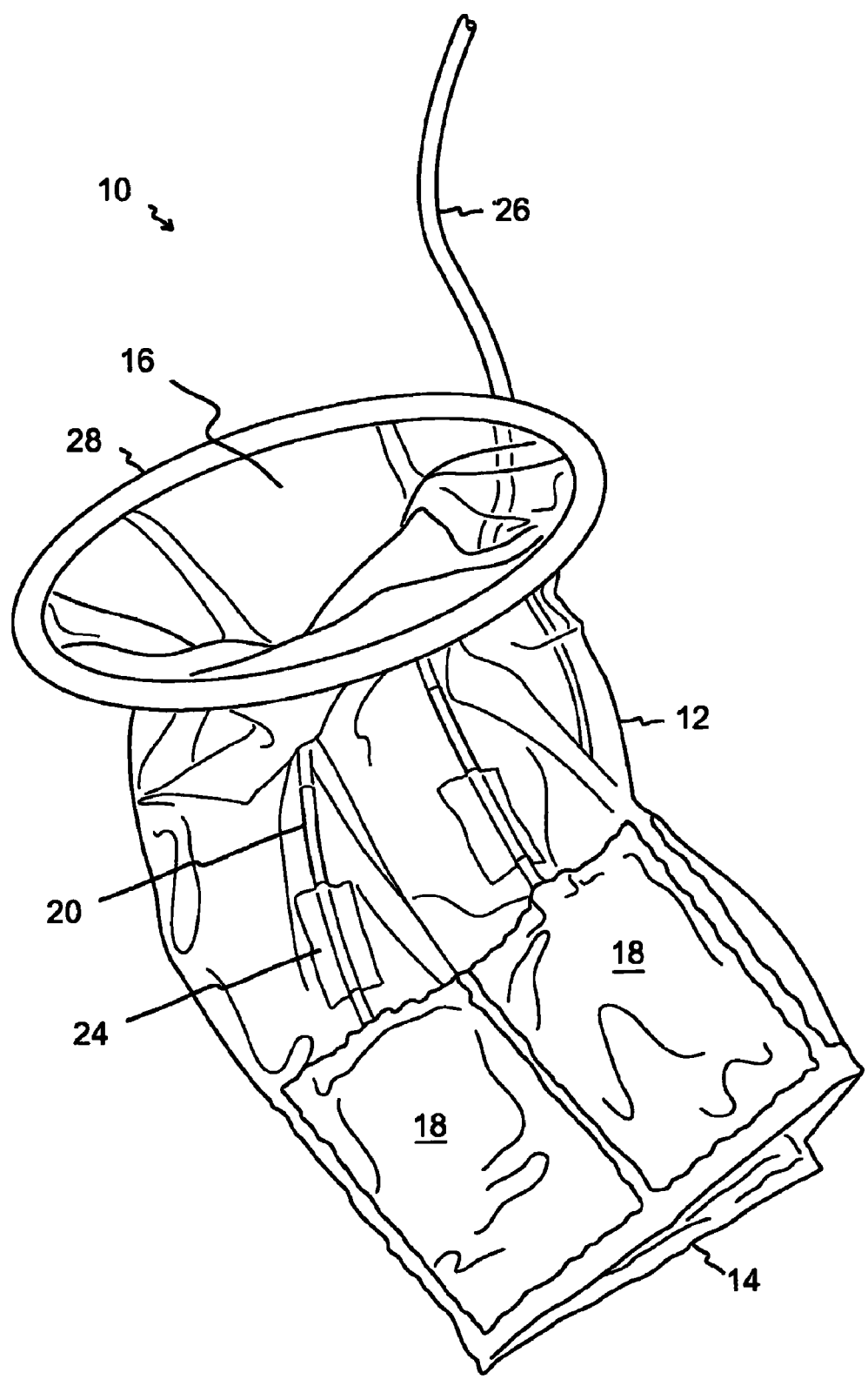
FIG. 1 illustrates a perspective view of a surgical device according to a preferred embodiment of the present invention, in which a number of distensible balloons thereon are in a collapsed state.
Figure 2:
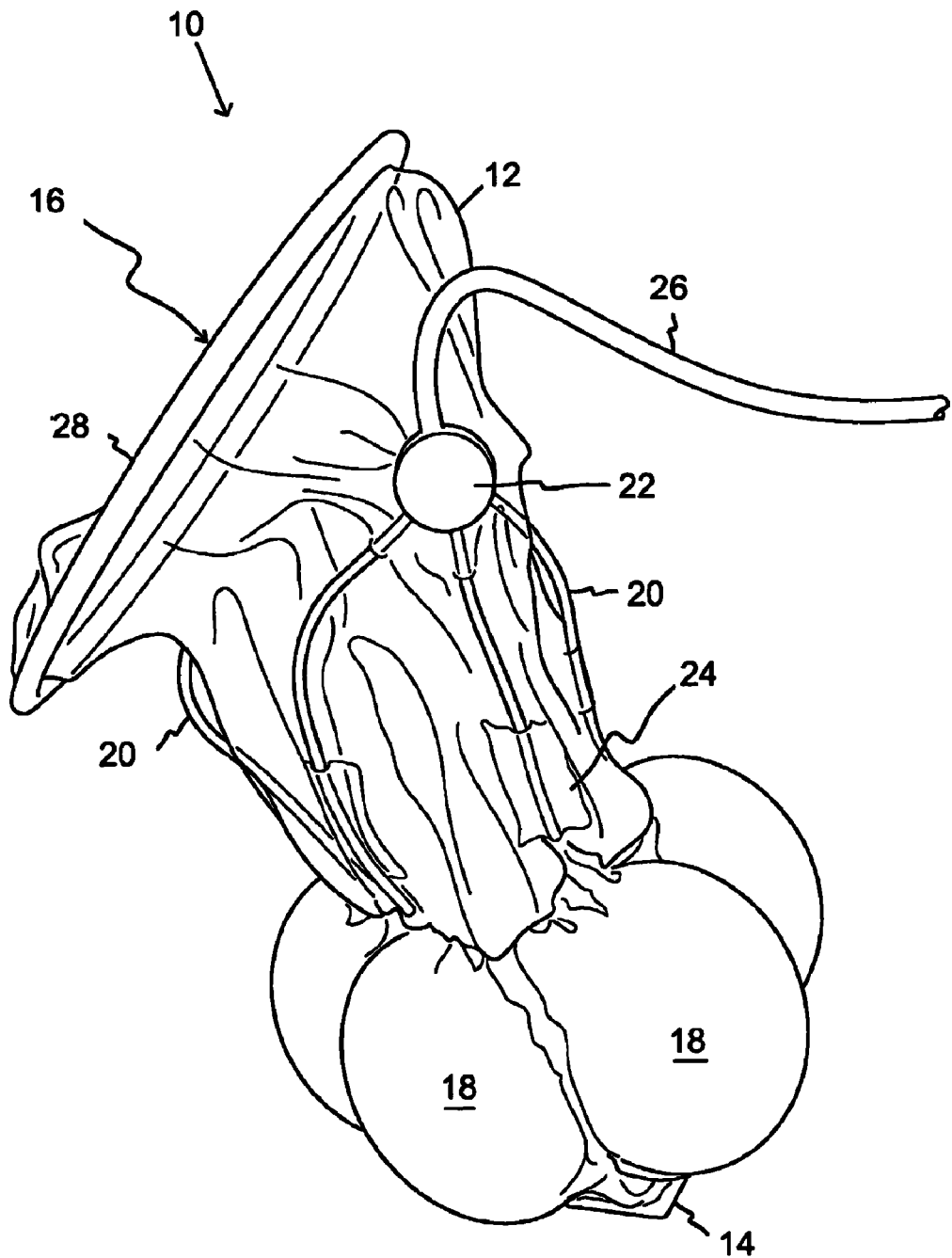
FIG. 2 illustrates a perspective view of the surgical device of FIG. 1, in which the distensible balloons have been inflated.
Figure 3:
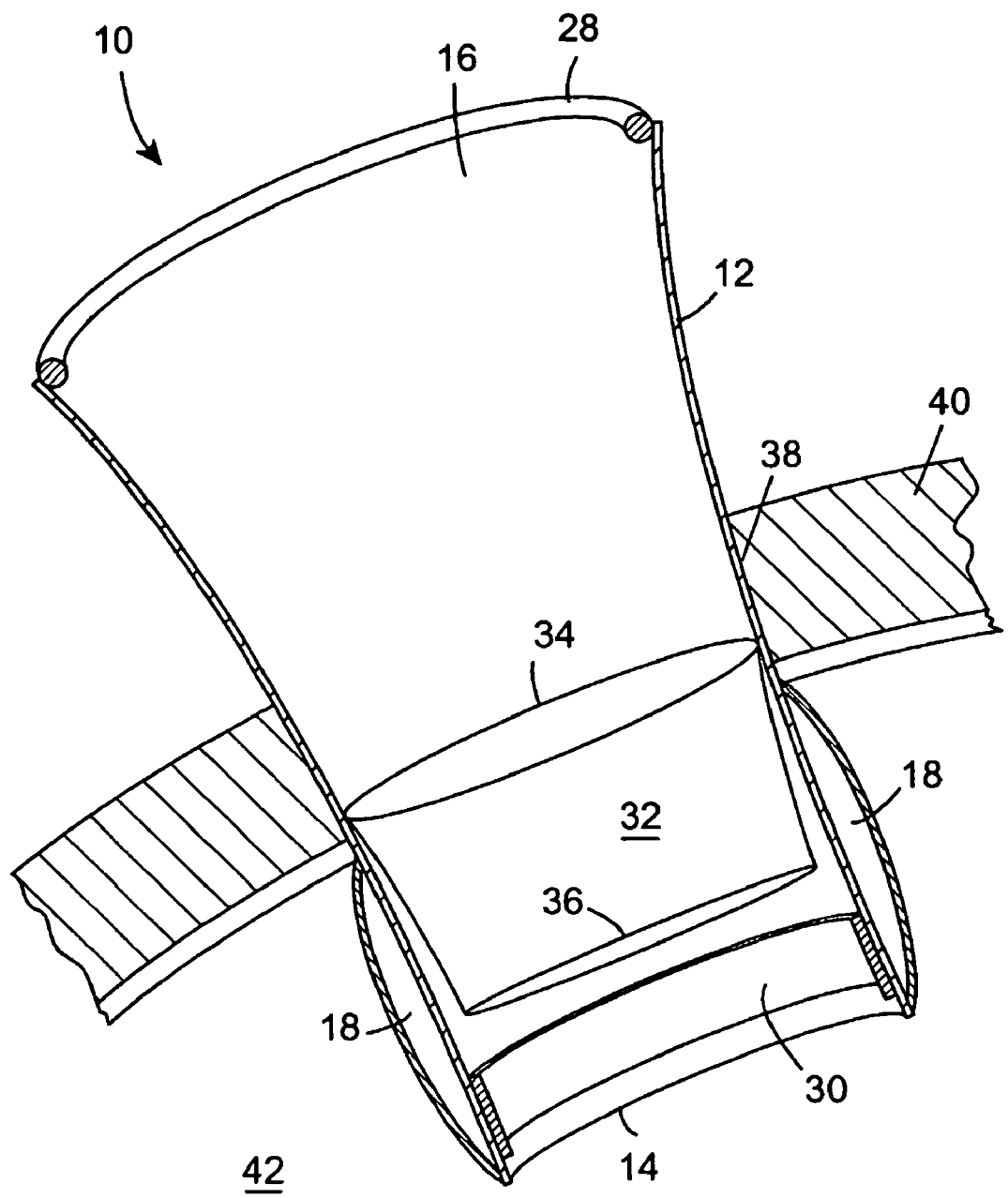
FIG. 3 illustrates a sectioned view of the surgical device of FIG. 1.

Referring now to the accompanying drawings, there is illustrated a surgical device, generally indicated as 10, for use in minimally invasive surgery such as hand assisted laparoscopic surgery, or any other form of surgery which involves the location of a surgeon's hand (not shown) within a restricted surgical cavity in order to perform a surgical procedure, in particular surgery within the abdominal cavity (schematically shown in FIG. 3).

The device 10 comprises a sleeve 12, preferably formed from a flexible material, the sleeve 12 having a exit aperture 14 for location, in use, at or adjacent a surgeon's wrist (not shown), and a entry aperture 16 for location, in use., at or adjacent the surgeon's elbow (not shown), or possibly shoulder (not shown). Located about the sleeve 12, adjacent the exit aperture 14, is a distensible member in the form of a plurality of balloons 18, in an annular array, secured to the exterior of the sleeve 12. Each of the balloons 18 are inflatable, as will be described in detail hereinafter. Thus, in use, a surgeon will pass his hand (not shown) in the entry aperture 16, along the interior of the sleeve 12, to exit at the exit aperture 14, such that the sleeve 12 surrounds some or all of the surgeon's forearm. Referring in particular to FIG. 3, the surgeon's arm (not shown), bearing the device 10, may then be inserted, at least partially, through a suitably dimensioned surgical incision 38, in a cavity wall 40, into a surgical cavity 42, for example the abdominal cavity or the like. Once the sleeve 12 is inserted a distance by which the balloons 18 are fully located within the cavity 42, as illustrated in FIG. 3, the balloons 18 may then be inflated in order to distend the area surrounding the surgeon's hand (not shown), in order to create a space within which the requisite surgical procedure may be performed, again as will be described in detail hereinafter.

The balloons 18 therefore facilitate the distension of the surgical cavity 42, for example the abdominal cavity, while avoiding the need to introduce a gas directly and continually into the cavity 42, thereby greatly simplifying, and reducing the cost of, any operation previously requiring such direct insufflation.

The sleeve 12 is preferably formed from a flexible material, in order to allow articulation of a surgeon's arm while wearing the device 10, and also to prevent damnage/injury to a patient (not shown) while the sleeve 12 is initially being inserted into the cavity 42, and again when being withdrawn therefrom. It will be appreciated that there are a large number of materials or combinations thereof, which would be suitable for use in manufacturing the sleeve 12. For example, the sleeve 12 could conceivably be formed from a fabric, but is preferably formed from a polymer, for example a medical grade polyurethane, as manufactured by Dow Corning, of Michigan, the United States.

As fibre optic cameras are typically employed during laparoscopic surgical procedures, the sleeve 12, and the balloons 18, are preferably transparent, in order to allow the full illumination of the cavity 42 created by distension of the balloons 18, in addition to permitting the visualisation of tissues/organs through the sleeve 12 and balloons 18. In addition, the sleeve 12 and balloons 18 are preferably liquid impermeable, in order to prevent the ingress of body fluids, in particular blood, into the interior of the sleeve 12, which might otherwise adversely affect the operation of the device 10. Furthermore, were an absorbent or a liquid permeable material employed, the device 10 would be significantly more difficult to clean/sterilise following each operation. However, the device 10 could be manufactured as a disposable item, to be discarded after a single use and, in that event, an absorbent or liquid permeable material could be employed.

The balloons 18 may also be formed from any suitable material, most preferably a medical grade polyurethane such as manufactured by Dow Corning, such polyurethane preferably being of a thickness of between 50 μm and 150 μm. Each of the balloons 18 are adhered to the exterior of the sleeve 12, in the preferred embodiment illustrated, by means of radio frequency welding. It will of course be appreciated that any other suitable means could be used, for example an adhesive or the like, to secure the balloons 18 to the sleeve 12. Alternatively, the balloons 18 could be formed integrally with the sleeve 12, which would therefore have to be formed, at least in the region of the balloons 18, from a suitably elastic or deformable material.

Although in the preferred embodiment illustrated, a plurality of the balloons 18 are provided, in one annular array, it will of course be apparent that a single annular balloon or bladder (not shown) could be provided about the sleeve 12, such a single balloon (not shown) preferably being annular or tubular in form, in order to completely circumscribe the sleeve 12. However, the use of a plurality of discrete balloons 18, as in the preferred embodiment illustrated, does provide a number of advantages. When inflated, the balloons 18, in addition to distending the surgical cavity 42, will exert a certain pressure on the surgeon's wrist. If this pressure were too great, movement of the surgeon's hand could be restricted, as could the flow of blood to the surgeons hand, which could of course adversely affect the surgeon's performance. However, as adjacent balloons 18 are inflated, they begin to press against one another, each balloon 18 therefore acting as an abutment for the adjacent balloon 18, thus limiting the pressure that the array of balloons 18 exert on the surgeon's wrist when disposed within the sleeve 12.

In addition, the use of individual balloons 18 means that each balloon 18 may be inflated independently, sequentially, or simultaneously, in order to suit the particular operation being performed. For example, with the sleeve 12 and balloons 18 located within the surgical cavity 42, it may be desired or necessary to distend only a particular portion of the cavity 42, or to distend one portion to a greater degree than another portion. In this case, the corresponding balloons 18 may be inflated or patially inflated, in order to suit the conditions in question. In order to effect inflation of the balloons 18, the device 10 includes a plurality of tubes 20, one being connected to each balloon 18, which tubes 20 are each in fluid-tight communication with a connector 22. In order to secure the various lengths of tube 20 to the sleeve 12, such as not to cause an obstruction during use of the device 10, a plurality of pockets 24 are provided on the exterior of the sleeve 12 at suitable locations, through each of which passes a single tube 20, in order to secure the tubes 20 in place. It will of course be understood that any other means could be employed in place of the pockets 24, in order to secure the tubes 20 in place. Extending from the connector 22 is a supply tube 26 which may be connected, in use, to a pump (not shown), or any other suitable gas supply (not shown) which may be selectively actuated in order to inflate one or more of the balloons 18. A one way valve (not shown) is preferably provided, either in each tube 20, within the connector 22, or in the supply tube 26, in order to prevent the balloons 18 from deflating during use. Alternatively, the fluid supply to the balloons 18 could be maintained at pressure during use of the device 10, in order to prevent deflation of the balloons 18. If a one way valve is provided, means must be provided to enable deflation of the balloons 18 subsequent to use of the device 10. It will also be apparent that some form of pump (not shown), such as a hand operated bladder or the like, could be provided on the device 10, in fluid communication with the balloons 18, in order to render the device 10 independent of external pumps or gas supplies.

It will also be understood that the plurality of balloons 18 could be in fluid communication with one another, thereby requiring only one of the tubes 20.

Thus, in use, the incision 38, for example between 5-11 cm in length, is made in the cavity wall 40, to provide access for the surgeon's hand. The incision 38 could be smaller, for example if using a robotic arm/hand (not shown), or could be made larger, depending on the size of the surgeon's hand. The surgeon then passes his hand through the sleeve 12, to exit at the exit aperture 14. The entry aperture 16 is preferably provided with a reinforcing member in the form of a rigid ring 28, secured to the sleeve 12, which serves to hold open the entry aperture 16. This therefore simplifies the insertion of the surgeon's hand into the sleeve 12, which will be of greater importance if the surgeon removes his arm from the sleeve 12 during an operation, and then has to re-insert his hand into the sleeve 12. Any other suitable arrangement may be employed in order to hold open the entry aperture 16, for example the use of a relatively stiff material for the portion of the sleeve 12 defining the entry aperture 16.

Referring to FIG. 3, the device 10 is preferably provided with a cuff 30 secured about the interior of the sleeve 12, adjacent the exit aperture 14. The cuff 30 is adapted to be lightly clamped about the surgeon's wrist during use, in order to ensure that the device 10 remains in the correct position relative to the surgeon's arm, preventing any relative movement therebetween. The cuff 30 is therefore preferably formed from an elasticated material, and again a fluid impermeable material is preferred.

Therefore, once the device 10 is secured in place on the surgeon's arm, the surgeon will pass his hand/wrist, bearing the sleeve 12, through the access incision 38 into the surgical cavity 42. Whilst at least that portion of the sleeve 12 carrying the balloons 18 will be inserted into the cavity 42, typically, only that portion of the sleeve 12 carrying the balloons 18 will be inserted into the surgical cavity, with the remainder of the sleeve 12 being located externally of the patient, as illustrated in FIG. 3. The supply tube 26 is then connected to a pump (not shown) or the like, and the balloons 18, or at least one thereof, inflated in order to distend the surgical cavity 42. The surgeon can therefore perform the necessary surgical procedure in the space created by distension of the balloons 18. During the course of the operation, one or more of the balloons 18 may be deflated or partially deflated, or alternatively inflated if not initially inflated, in order to alter the shape/size/location of the cavity 42 created, in order to provide access to various areas within the surgical cavity 42.

It will be appreciated that there will be very limited space within the cavity 42, for example the abdominal cavity, into which the surgeon's hand may be located, prior to distension of the cavity 42 using the balloons 18. It is for this reason that the balloons 18 should be located as close as possible to the exit aperture 14, such that the surgeon need only pass his hand/wrist into the cavity 42 before the balloons 18 can be inflated. The balloons 18 are therefore preferably dimensioned to extend only a short length, for example 5 cm-10 cm, back from the exit aperture 14, in order to minimise the distance into the surgical cavity 42 the surgeon need insert his hand/wrist, before inflation of the balloons 18 can occur. The sleeve 12 may also be positioned on the surgeon's arm such that the exit aperture 14 is located about the upper or metacarpal portion of the surgeon's hand, in order to further reduce the level of insertion of the sleeve 12 required before inflation of the balloons 18, provided that such positioning is not prohibitively restrictive for the surgeon. In the preferred embodiment illustrated, the sleeve 12 is of a length sufficient to extend, in use, approximately halfway up the surgeon's forearm, with the balloons 18 extending approximately 6 cm-8 cm rearwardly along the sleeve 12 from the exit aperture 14, again to minimise the proportion of the sleeve 12 which must be accommodated within the cavity 42 before inflation of the balloons 18 can occur.

As an alternative, the balloons 18 could be replaced with two or more parallel, circumferentially disposed arrays or rows of balloons (not shown) of shorter length than the balloons 18 of the embodiment illustrated. Such an arrangement would therefore comprise a first row (not shown) of balloons disposed about the exit aperture 14, and a similar second row (not shown) of balloons disposed adjacent the first row, in parallel thereto, with the possibility of having a third and subsequent row disposed along the sleeve 12. In this way, the sleeve 12 could be inserted into the surgical cavity 42 a distance sufficient to locate the first row of balloons within the cavity 42. The first row could then be inflated, thereby distending the cavity 42, allowing the surgeon to advance his hand/wrist further into the cavity 42, until the second row of balloons is located within the cavity 42. The second row would then be inflated, further distending the cavity 42. This process could be repeated with third and subsequent rows until the desired level of distension of the cavity 42 was achieved.

Alternatively, the portion of the sleeve 12 carrying the balloons 18, and the balloons 18 themselves, both being of a flexible material, could be compressed/collapsed against the surgeon's hand/wrist, in order to minimise the length of same, and then passed through the incision 38 into the cavity 42. The balloons 18 could then be inflated as normal.

As explained above, during the course of an operation, it is likely that the surgeon will have to remove his arm/forearm from within the surgical cavity 42, for one reason or another. It is however likely to be preferable to leave the device 10 in place, and to simply slide the surgeon's hand rearwardly out of the sleeve 12, via the entry aperture 16. In order to aid in removal of the surgeon's hand from the device 10, the interior of the sleeve 12 is preferably provided with a coating of a lubricant, for example a KY® gel, which will therefore facilitate smooth and resistance free removal, and re-insertion, of the surgeon's hand into the sleeve 12. Such a lubricant will therefore assist in preventing the sleeve 12 from being inadvertently drawn partially or fully out of the surgical cavity 42 as the surgeon's arm is removed from same.

When using the device 10, it may exceptionally be desirable to add additional insufflation gas directly into the surgical cavity 42, although this is not required. In such a case, when the surgeon desires to remove his arm from within the sleeve 12 during the surgical procedure, it is necessary to prevent said insufflation gases from leaking out of the surgical cavity 42 through the sleeve 12. A sealing cap (not shown) may therefore be provided, which can be secured about the ring 28, in order to create a fluid tight seal with the sleeve 12, thereby preventing escape of the insufflation gases. With such an arrangement, the entire sleeve 12 will have to be fluid tight, in order to prevent the leaking of gas therethrough. As an alternative, and referring to FIG. 3, sealing means in the form of a one way mitral valve 32 may be provided on the interior of the sleeve 12, the valve 32 being configured to allow access from the entry aperture 16 to the exit aperture 14, but not fluid flow in the reverse direction. Thus, when the surgeon's hand is removed from the sleeve 12, the valve 32 will prevent escape of the insufflation gas from the sleeve 12.

The valve 32 is of flexible tubular form, having a first end or inlet 34 which is secured, about the entire circumference thereof, to the interior of the sleeve 12, and a second end or outlet 36 which is freely suspended within the sleeve 12. The flexibility of the valve 32, in addition to the dimensions thereof, allow the surgeon's hand to be passed through same, such that the valve 32 does not cause an obstruction as the surgeon's hand is being passed through the sleeve 12. The valve 32 functions by having the inlet 34 secured against the sleeve 12, thereby holding the inlet 34 open at all times. Thus a fluid such as a gas travelling from the entry aperture 16 towards the exit aperture 14 will enter the valve 32 via the open inlet 34, the pressure of the gas forcing open the outlet 36, in order to allow the passage of the gas through the valve 32. However, if the flow of gas is reversed, the outlet 36 is not held open like the inlet 34, and thus the pressure of the gas causes the valve 32 to collapse in on itself, thereby closing the outlet 36 and preventing the passage of gas through the valve 32 in this direction. In order to prevent the valve 32 from being turned inside out, whether due to excessive pressure on same, or during withdrawal of the surgeon's arm from within the sleeve 12, the valve 32 is preferably secured to the sleeve 12 along one or more, preferably two diametrically opposed, longitudinal seams (not shown) extending from the inlet 34 to the outlet 36. These seams (not shown) therefore serve to secure the valve 32 in place, without interfering with the collapsible nature of the valve 32, in particular the outlet 36. The valve 32 therefore provides a simple yet effective means of preventing the escape of insufflation gases through the sleeve 12. It will of course be appreciated that any suitable alternative to the valve 32 could be employed, provided that the functionality of the valve 32 is maintained.

When the surgeon's arm is located within the sleeve 12, the cuff 30 is lightly clamped against the surgeon's wrist, thereby preventing the escape of insufflational gases past the surgeon's wrist and through the sleeve 12.

Once the surgical procedure has been completed, the balloons 18 are deflated so that the surgeon's arm and the sleeve 12 are easily removed from within the surgical cavity 42. The device 10 may then be cleaned and sterilised as required, in readiness for the next procedure, or simply discarded if produced as a disposable item.

As mentioned above, it is conventional practice, and typically essential, to use a fibre optic camera (not shown) or the like, during laparoscopic surgical procedures. The device 10 is therefore preferably provided with means (not shown) for guiding a fibre optic camera (not shown) down the length of the sleeve 12, in order to exit at or adjacent the exit aperture 14, thereby allowing the clear visualisation of the surgeon's hand during any surgical procedure. The guiding means (not shown) could for example take the form of a simple tube (not shown) running along the length of the sleeve 12, on the inside or outside thereof, the tube being dimensioned to receive a fibre optic camera or the like.

The surgical device 10 of the present invention thus provides a means by which insufflation gases are contained within a reservoir, in particular the balloons 18. Thus the cost and complexity associated with a continual leakage of gas from the cavity are avoided. Furthermore, when the device is employed without the use of insufflation gases, which will be the normal mode of operation, adverse reactions and complications associated with introducing $CO_2$ or the like directly into the abdominal cavity can be avoided.

The invention claimed is:

1. A surgical device for use in minimally invasive surgery and having a portion insertable through a surgical incision in a wall of a surgical cavity and within the surgical cavity, the device comprising a sleeve having an exit aperture and an entry aperture, the sleeve being shaped and dimensioned to permit the passage of a hand therethrough; and a distensible member secured to or formed integrally about the sleeve adjacent the exit aperture; wherein the distensible member is positioned on the sleeve to be locatable, in use, through the surgical cavity wall and internally within the surgical cavity, and is sufficiently distensible to distend the surgical cavity an amount which will allow hand assisted surgery to be performed within the surgical cavity without the use of insufflation gas inserted in the surgical cavity.

2. A surgical device according to claim 1 in which the distensible member is generally annular in form and is located circumferentially about the sleeve adjacent the exit aperture.

3. A surgical device according to claim 1 in which the distensible member comprises a plurality of distensible sections arranged in an annular array or in a series of annular arrays adjacent the exit aperture.

4. A surgical device according to claim 3 in which the plurality of distensible sections may be individually, sequentially or simultaneously distended.

5. A surgical device according to claim 1 in which the distensible member is secured to an exterior of the sleeve and is arranged to distend away from the arm, in use.

6. A surgical device according to claim 1 in which the entry aperture has a larger cross sectional area than the exit aperture.

7. A surgical device according to claim 1 in which the sleeve is substantially frustum shaped.

8. A surgical device according to claim 1 in which the sleeve is formed from a flexible material.

9. A surgical device according to claim 1 in which the sleeve is shaped and dimensioned to permit the passage of a surgeon's hand therethrough and to accommodate at least a surgeon's forearm, in use.

10. A surgical device according to claim 1 in which the sleeve is formed from a fluid impermeable material.

11. A surgical device according to claim 1 in which the device further comprises a reinforcing member located about the entry aperture of the sleeve, in order to hold open the entry aperture.

12. A surgical device according to claim 1 in which the device comprises means operable to seal the exit aperture from the entry aperture.

13. A surgical device according to claim 12 in which the sealing means comprises a one way valve.

14. A surgical device according to claim 1 in which the sleeve is provided with a lubricant on an interior surface thereof.

15. A surgical device according to claim 1 in which the device further comprises means for conveying a fibre optic camera along the length of the sleeve.

16. A surgical device according to claim 15 in which the conveying means comprises a passage extending along the length of the sleeve.

17. A surgical device according to claim 1 in which the device further comprises a cover releasably securable about the entry aperture, in order to fluid-tightedly seal the entry aperture.

18. A surgical device according to claim 1 in which the sleeve is substantially transparent.

19. A surgical device according to claim 1 in which the device further comprises a cuff located circumferentially or annularly about the sleeve adjacent the exit aperture of the sleeve.

20. A method of distending a surgical cavity, the method comprising the steps of;
    providing a surgical device according to claim 1;
    passing a hand through the sleeve of the device;
    inserting at least the distensible member of the device through the surgical incision in the wall of the surgical cavity and into the surgical cavity; and
    distending the distensible member an amount which will allow hand assisted surgery to be performed within the surgical cavity.

* * * * *